United States Patent [19]

Eisner et al.

[11] Patent Number: 4,907,968
[45] Date of Patent: Mar. 13, 1990

[54] DENTAL SYRINGE SHIELD OR PROPHYLACTIC

[76] Inventors: Mark R. Eisner, 2895 Hamilton Blvd., Ste 205, Allentown, Pa. 18104; Charlton D. Becker, 321 Barrett Rd., Emmaus, Pa. 18049

[21] Appl. No.: 190,816

[22] Filed: May 6, 1988

[51] Int. Cl.[4] ............................................. A61G 17/02
[52] U.S. Cl. ...................................... 433/80; 433/116
[58] Field of Search .................. 433/80, 116; 604/110; 128/9, 23

[56] References Cited

U.S. PATENT DOCUMENTS

| | | | |
|---|---|---|---|
| 1,691,823 | 11/1928 | Ogilvie | 433/116 |
| 2,073,137 | 3/1937 | Bimrose | 433/116 |
| 3,794,091 | 2/1974 | Ersek et al. | 128/23 |
| 3,878,836 | 4/1975 | Twentier | 128/9 |
| 4,248,589 | 2/1981 | Lewis | 433/80 |
| 4,795,343 | 1/1989 | Choisser | 433/132 |
| 4,810,194 | 3/1989 | Snedden | 433/116 |

Primary Examiner—John J. Wilson
Attorney, Agent, or Firm—Sanford J. Piltch

[57] ABSTRACT

A dental syringe covering, shield or prophylactic comprised of a thin, tear-resistant, but deformable material which is sterile and disposable for covering the exposed nozzle surfaces of different types of dental syringes providing a covering which will significantly reduce and/or prevent the spread of diseases which may be transmitted by or through contact with human body fluids and tissues during dental procedures.

21 Claims, 2 Drawing Sheets

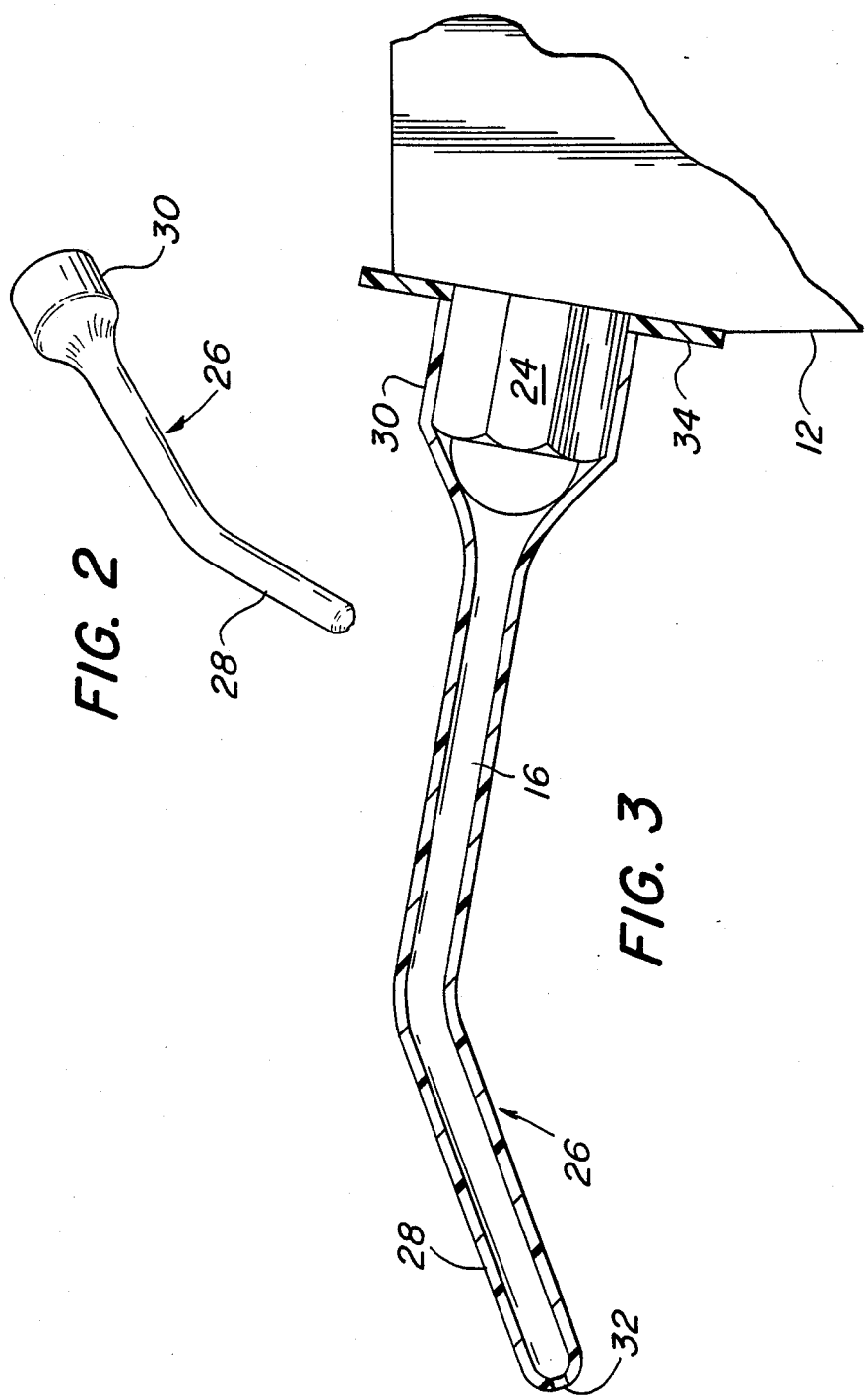

DENTAL SYRINGE SHIELD OR PROPHYLACTIC

BACKGROUND OF THE INVENTION

Dental practitioners have been aware for years that the repeated touching of the dental syringe by gloved or ungloved hands after a dental practitioner's, or the hygienist's hands have been in or around the mouths of several different patients without sterilization can bring about the spread of contagious diseases. Such contagious or communicable diseases are borne in or on the body fluids and/or tissues which become attached to the exterior surfaces of the syringe or of the gloved or ungloved hands of the dental practitioner or hygienist and are transmitted to the syringe through contact. More recently the spread of the Hepatitus virus and the Acquired Immune Deficiency virus have caused great concern for dental practitioners, hygienists and other dental office staff, not only for their patients, but also for their own health and well-being.

Both the Hepatitus virus and the Acquired Immune Deficiency virus can be carried in or on body fluids and/or tissues. In the environment in which dental practitioners and hygienists work, i.e. inside the mouth, body fluids such as saliva, blood, etc. and the tissues comprising the gum and portions of the teeth, the pulp and root, may potentially transmit the virus through contact. The process of cleaning and/or repairing teeth by filing caries or performing a root canal procedure requires the drilling of the teeth and the subsequent scattering of tissue particles and body fluids about the mouth. Some of those particles and/or fluids become attached or adhere to the surfaces of the syringe and to the gloved or ungloved hand of the dental practitioner or hygienist. Cleaning and sterilizing the syringe between patients has been a serious problem for dental practitioners and hygienists because of their construction and lack of ease in removing and remounting.

During the dental procedures ranging from filling caries to cleaning teeth, the syringe is continually used to expel or dislodge tissue particles from, and to rinse the work area in the interior of the patient's mouth by introducing a stream or spray of water to the area. The syringe may be inserted into the patient's mouth to direct its stream or spray to a particularly difficult to reach work area. When so inserted, the backsplash of tissue particles and/or body fluids may become attached to the surfaces of the syringe. Anything the syringe may have come into contact with while in the patient's mouth can be transmitted to others by mere contact with the syringe. Little has been done to improve the level of sterilization for syringes used in the dental operatory.

The dental syringe, however, is not usually thought of as a disease transmission device. It is usually cleaned by wiping down with a disinfectant liquid or spray, but not sterilized. The sterilization of a dental syringe, which could fit in a large sterilization chamber, requires the disassembly of the syringe from its connecting tubes and cables and the remounting after sterilization. As a stopgap measure, the dental syringe has been sprayed with a disinfecting agent but such practice does not reduce or eliminate bacteria or virus forms on the syringe. This spraying may be performed between successive patients, but usually does not occur more than possibly once or twice a day. Thus, disinfecting of the dental syringe does not normally occur between each patient and certainly does not occur between either interior mouth contact or hand contact with the syringe by the dental practitioner, hygienist or other staff members during the performing of dental procedures on a patient.

In recent years dental practitioners have become increasingly aware of the rapid spread of communicable diseases through contact with body fluids and tissues such as may be dislodged and/or become attached to the surfaces of the syringe or to the gloved or ungloved hands of the dental practitioner or hygienist during procedures in the mouth of a patient. In fact, dental practitioners, along with dental hygienists, have been cautioned to protect themselves from infection by using sterile gloves and masks and to use protective glasses when practicing dentistry or other dental procedures on their patients. Very recently the rapid spread of the Hepatitus virus and the Acquired Immune Deficiency virus has caused significant concern among dental practitioners and hygienists. The American Dental Association and other professional organizations have strongly urged that dental practitioners and hygienists take additional steps to decrease the chance of spreading the disease through the use of non-sterile implements.

It is therefore an object of the present invention to provide a sterile protective covering or shield for the dental syringe to significantly reduce or prevent the spread of contagious, communicable diseases.

It is a further object of the present invention to provide such a shield which is disposable after a single use and which is easily applied and removed so that it will have wide-spread acceptance in the dental professions.

It is another object of the present invention to provide such a shield with a backsplash collar to prevent particulate matter, e.g. tissues or body fluids, from splashing out of the mouth of the patient during rinsing of work areas.

It is still another object of the present invention to provide a shield which is sufficiently elastic, yet tear resistant, and which is capable of covering the entirety of a variety of differently shaped dental syringes.

Other objects will appear hereinafter.

SUMMARY OF THE INVENTION

The dental syringe covering, shield or prophylactic of the present invention is comprised of a thin, tear-resistant, but deformable material which is sterile and disposable for covering the exposed nozzle surfaces of different types of dental syringes.

The present invention is an apparatus for significantly reducing or preventing the spread of communicable diseases which may be transmitted by or through contact with human body fluids and tissues during dental procedures. The apparatus comprises a removable disposable sterile dental syringe shield or prophylactic for placement over and in proximate contact with the nozzle of a dental syringe. The shield is used to significantly reduce the spread of communicable diseases which may be transmitted by or through contact with human body fluids and tissues during a first and subsequent uses of the dental syringe in conjunction with the treatment of two or more patients.

The covering, shield or prophylactic is comprised of an elongated cylindrical portion for fitting over the nozzle of the dental syringe and a barrel portion for fitting over the nozzle securing means of the dental syringe. The internal dimensions of the shield are just slightly larger than the external dimensions of the nozzle and nozzle securing means in order to provide a snug fit and to maintain the shield in place during use. The shield is further comprised of a backsplash collar shield means, which fits over the nozzle portion and abuts the front of the base portion of the dental syringe. The backsplash collar shield prevents body tissues and/or fluids expelled from the mouth of a patient from attaching or adhering to other parts of the dental syringe. The backsplash collar shield may be circular or substantially hemispheric in shape and has a central aperture for fitting over the nozzle securing means of the dental syringe.

The backsplash collar shield is preferred to have a radius with an upper range of approximately two inches. The shield is made from a thermoplastic, vinyl, latex, rubber, elastomeric, or other polymer-type material, or any combination thereof, natural or man-made which exhibits sufficient deformability to conform to the particular shape of the shield and toughness and/or tear resistance to withstand pulling and stretching during application and/or removal.

Additionally, aseptic medicaments, talc and/or lubricants may be applied to the inner surface of the shield for continued disinfection and for lubrication in the application and removal of the shield. It is also preferred that the outer surface of the shield has a medium to high degree of frictional contact.

BRIEF DESCRIPTION OF THE DRAWINGS

For the purpose of illustrating the invention, there is shown in the drawings a form which is presently preferred; it being understood, however, that the invention is not limited to the precise arrangement and instrumentalities shown.

FIG. 2 is an isometric view of the shield or prophylactic of the present invention.

FIG. 3 is a partial cutaway view of the shield or prophylactic of the present invention applied to the nozzle portion of the dental syringe with a backsplash collar shield.

DETAILED DESCRIPTION OF THE INVENTION

Figure 1:
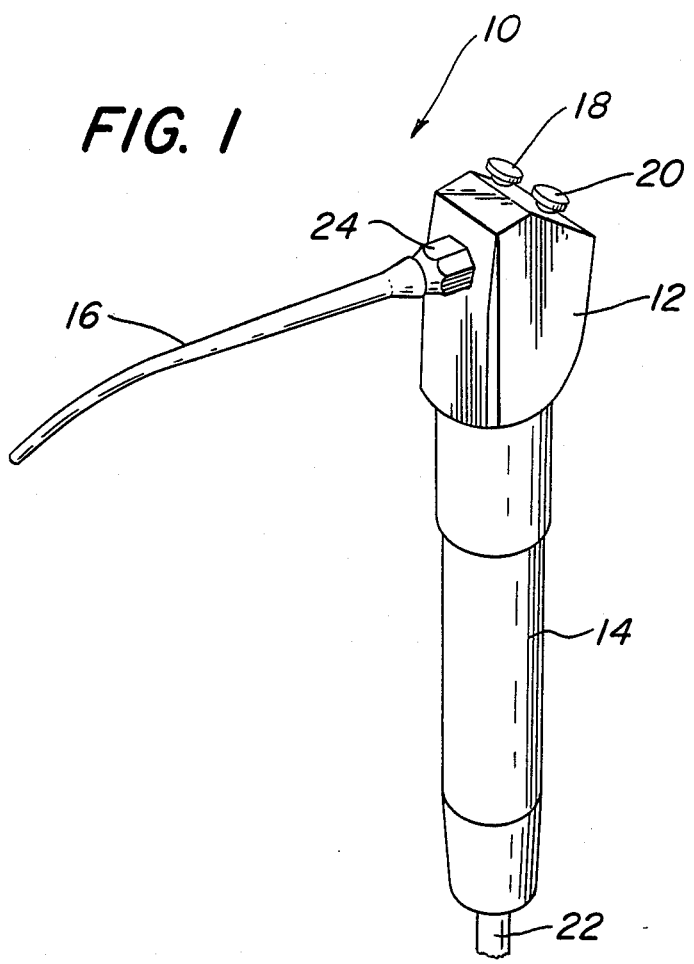
FIG. 1 is an isometric view of a dental syringe having body, handle and nozzle portions.

The following detailed description is of the best presently contemplated mode of carrying out the present invention. This description is not intended in a limiting sense, but is made solely for the purpose of illustrating the general principles of the invention.

Referring now to the drawings in detail, wherein like numerals represent like elements, there is shown in FIG. 1 a dental syringe 10 for use in expelling, dislodging and/or rinsing away particulate material, such as body tissue, and/or body fluids from a work area interior to the mouth of a patient. The dental syringe 10 has three major parts: a base portion 12, a handle portion 14 and a nozzle portion 16. The base portion 12 connects the handle portion 14 and the nozzle portion 16 and provides control over the expulsion of compressed air, pressurized water, or a mixture of both through the nozzle 16. Each of the buttons 18, 20 control the flow of the compressed air or the pressurized water through the nozzle 16 by the dental practitioner, hygienist or other dental staff member by pressing downward on them.

The compressed air and pressurized water is brought to the base 12 of the syringe 10 through a multi-tubed flexible hose 22 which is connected to the syringe control unit (not shown). The hose 22 is connected through the handle portion 14 of the syringe 10 terminating in two miniature valves controlled by the buttons 18, 20. When the buttons 18, 20 are extended upward the valves are closed. Any downward pressure exerted on the buttons 18, 20 provides a flow path for the compressed air or pressurized water through the respective valve and into the nozzle 16.

The nozzle 16, which has a small central bore throughout its entire length, is connected to the front of the base portion 12 through a port which provides for the mixing of the fluid flows from both of the miniature valves, as controlled by the buttons 18, 20. This mixing port provides a fluid flow path to the nozzle 16 from either or both of the miniature valves, individually or simultaneously. The nozzle 16 is affixed to the front of the base 12 by a securing nut 24 which puts the proximal end of the nozzle 16 in contact with the output of the mixing port. The connection of the nozzle 16 to the base 12 is constructed so as to provide for rotation of the nozzle 16 without loss of integrity of the fluid flow path. The nozzle 16 may be curved or angled as shown in the drawing to achieve greater manuverability and control over the stream or spray in the close quarters within a patient's mouth. The syringe just described is commercially available from several dental equipment manufacturers, e.g. ADEC and Kent.

The handle 14 and the nozzle 16 are manipulated by the dental practitioner, dental hygienist, or other dental staff member to expel, dislodge or rinse away particulate material, especially body tissue and/or fluids from the work area within the patient's mouth in and around the teeth and gums. The dental practitioner or hygienist may make adjustments to the particular rotational angle of the nozzle 16 in order to achieve a specific direction of flow for the compressed air/pressurized water mixture. It is normal practice to use the dental syringe 10 and to adjust the nozzle 16 several times during a dental procedure, especially if the procedure requires the removal of a portion of a tooth or the removal of the pulp or a root of a tooth. If the gloved or ungloved hand of the dental practitioner or other member of the staff had contacted infected tissue or body fluid, or if infected tissue or body fluid had become attached to the syringe 10, the entire syringe has become non-sterile by such contact. The same holds true for any bacteria normally found within the mouth of a human if it comes into contact with the syringe 10. The chance of passing such bacteria, or virus form, to another patient during subsequent use of the the syringe on another patient without complete sterilization of the syringe is significant and highly probable.

Referring now to FIGS. 2 and 3, the preferred embodiment of the shield or prophylactic of the present invention is shown. The shield 26 is shaped to generally conform to the curved or angled nozzle 16 of the syringe 10. The shield 26 may be formed from any thermoplastic, vinyl, latex, rubber, elastomeric, or other polymer-type material, natural or man-made which exhibits sufficient deformability to adapt to any of a variety of angular or curved shapes of the nozzle 16 of the dental syringe 10. The shield 26 must also exhibit a sufficient toughness and/or tear resistance to withstand pulling and stretching during application and/or removal of the shield from the nozzle portion 16 of the syringe 10. The outer surface of the shield 26 is preferred to have a medium to high degree of frictional contact to provide sufficient firmness of grasp to adjust the angle of the nozzle 16 during dental procedures where hands, gloved or ungloved, may be wet or damp from body fluids or otherwise.

The shield 26 comprises an elongated cylindrical tip portion 28 for fitting over the nozzle 16 and a barrel portion 30 for fitting over the securing nut 24. The shield 26 fits snugly over the nozzle 16 and the securing nut 24 so as to abut against the front of the base 12 of the syringe 10. The internal dimensions of the shield are preferred to be just slightly larger than the external dimensions of the nozzle 16 and the securing nut 24. At the distal end of the shield 26 is an opening 32 which continues the fluid flow path permitting the compressed air and pressurized water mixture to be directed to a specific work area without unwanted deflection. Once the shield 26 is slid into place over the nozzle 16 and the securing nut 24, it will remain in place until removed. Thus, the disinfected, and substantially sterile, condition of the dental syringe can be maintained by the timely application and removal of the shield 26.

To further the efforts to maintain a substantially sterile environment about the dental syringe 10, asceptic medicaments, talc and/or lubricants may be applied to the internal surface of the shield 26 for continued disinfection and lubrication in the application and removal of the shield.

Additionally, a backsplash collar shield 34 may be added to the shield 26 of the present invention. This backsplash collar shield 34, as shown in FIG. 3, is a flat, circular piece of thermoplastic, vinyl, latex, rubber, elastomeric, or other polymer-type material, natural or man-made, which has a central aperture for fitting over the securing nut 24. The backsplash collar shield 34 is placed against the front of the base 12 of the syringe 10 to prevent any body tissues and/or fluids from attaching to the base 12 or handle 14 of the syringe 10 if expelled from the mouth of the patient. The backsplash collar shield 34 is held firmly in place against the base 12 by the fully applied shield 26. When used, the backsplash collar shield 34 can be of assistance in removing the shield 26 from the syringe 10. The backsplash collar shield 34 can be configured in a variety of different shapes to provide for the deflection of body tissues and/or fluids from attaching to the base 12 or handle 14 of the syringe 10. Examples of some acceptable shapes are concave or convex partial spheres extending outward from a center point a preferred distance of two to three inches. Either of these may be substituted for the backsplash shield 34 shown in FIG. 3. Alternatively, instead of a separate backsplash collar shield 34, the shield 34 may be formed and/or incorporated as part of the shield 26 as a single piece.

The shield or prophylactic 26 of the present invention can be used with all types of dental syringes having small bore curved or angled nozzles. The present invention provides a significant step forward in reducing the rapid spread of contagious, communicable diseases of the Hepatitus and Acquired Immune Deficiency viral type which are borne in or on the body fluids and tissues of humans. The shield or prophylactic 26 provides a substantially sterile surface on the exterior of the dental syringe 10 which, without a shield, would be a likely place for the harboring or transmittance of such diseases. The backsplash collar shield 34 enhances the ability to maintain a disinfected, and substantially sterile, surface on the syringe 10, especially on the base portion 12 and handle portion 14 thereof. The shields 26 and 34 are contemplated to be used for a single patient and then discarded. New sterile shields 26 and/or 34 would be applied to the syringe for use with a subsequent patient.

The present invention may be embodied in other specific forms without departing from the spirit or essential attributes thereof and, accordingly, reference should be made to the appended claims, rather than to the foregoing specification, as indicating the scope of the invention.

I claim:

1. A removable disposable dental syringe covering, shield or prophylactic for placement over and in proximate contact with the nozzle of a dental syringe for significantly reducing the spread of communicable diseases which may be transmitted by or through contact with human body fluids and tissues during a first and subsequent uses of the dental syringe in conjunction with the treatment of two or more patients comprising an elongated cylindrical portion for fitting over the nozzle of the dental syringe and a barrel portion for fitting over the nozzle securing means of the dental syringe, and further comprising a backsplash collar shield means, which fits over the nozzle portion and abuts the front of the base portion of the dental syringe, for preventing body tissues and/or fluids expelled from the mouth of a patient from attaching or adhering to other portions of the dental syringe.

2. In accordance with claim 1 wherein the internal dimensions of the shield are just slightly larger than the external dimensions of the nozzle and nozzle securing means in order to provide a snug fit and to maintain the shield in place during use.

3. In accordance with claim 2 wherein asceptic medicaments, talc and lubricants are applied to the inner surface of the shield for continued disinfection and for lubrication in the application and removal of the shield.

4. In accordance with claim 1 wherein the outer surface of the shield has a medium to high degree of frictional contact.

5. In accordance with claim 1 wherein the shield is made from a material selected from the group consisting of thermoplastics, vinyls, latexes, rubbers, elastomerics, or other polymer-type materials, natural or man-made, or any combination thereof.

6. In accordance with claim 5 wherein said material exhibits sufficient deformability to conform to the particular shape of the dental syringe nozzle and nozzle securing means and toughness or wear-resistance to withstand pulling and stretching during application and removal.

7. In accordance with claim 1 wherein said backsplash collar shield means is circular in shape having a central aperture for fitting over the nozzle securing means of the dental syringe.

8. In accordance with claim 1 wherein said backsplash collar shield means is substantially hemispheric in shape having a central aperture for fitting over the nozzle securing means of the dental syringe.

9. In accordance with claim 1 wherein said backsplash collar shield means has a radius with an upper range of two inches.

10. In accordance with claim 1 wherein one or more additives selected from the group consisting of asceptic medicaments, talc, and lubricants are applied to the inner surface of the shield for continued disinfection and for lubrication in the application and removal of the shield.

11. In combination, a dental syringe having a nozzle and a nozzle securing means and a removable disposable covering, shield or prophylactic removably fitted over and in proximate contact with the nozzle and nozzle securing means of the dental syringe for significantly reducing the spread of communicable diseases which may be transmitted by or through contact with human body fluids and tissues during a first and subsequent uses of the dental syringe in conjunction with the treatment of two or more patients, said shield comprising an elongated cylindrical portion for fitting over the nozzle and a barrel portion of larger diameter for fitting over the nozzle securing means.

12. In accordance with claim 11 wherein the internal dimensions of the shield are just slightly larger than the external dimensions of the nozzle and the nozzle securing means in order to provide a snug fit and to maintain the shield in place during use.

13. In accordance with claim 11 wherein asceptic medicaments, talc, and lubricants are applied to the inner surface of the shield for continued disinfection and for lubrication in the application and removal of the shield.

14. In accordance with claim 1 wherein one or more additives selected from the group consisting of asceptic medicaments, talc, and lubricants are applied to the inner surface of the shield for continued disinfection and for lubrication in the application and removal of the shield.

15. In accordance with claim 11 wherein the outer surface of the shield has a medium to high degree of frictional contact.

16. In accordance with claim 11 wherein the shield is made from a material selected from the group consisting of thermoplastics, vinyls, latexes, rubbers, elastomerics, or other polymer-type materials, natural or man-made, or any combination thereof.

17. In accordance with claim 16 wherein said material exhibits sufficient deformability to conform to the particular shape of the dental syringe nozzle and nozzle securing means and toughness or tear-resistance to withstand pulling and stretching during application and removal.

18. In accordance with claim 11 wherein the shield or prophylactic further comprises a backsplash collar shield means, which fits over the nozzle portion and abuts the front of the base portion of the dental syringe, for preventing body tissues and/or fluids expelled from the mouth of a patient from attaching or adhering to other portions of the dental syringe.

19. In accordance with claim 18 wherein said backsplash collar shield means is circular in shape having a central aperture for fitting over the nozzle securing means of the dental syringe.

20. In accordance with claim 18 wherein said backsplash collar shield means is substantially hemispheric in shape having a central aperture for fitting over the nozzle securing means of the dental syringe.

21. In accordance with claim 18 wherein said backsplash collar shield means has a radius with an upper range of two inches.

* * * * *